(12) United States Patent
Hashimoto et al.

(10) Patent No.: US 10,307,657 B2
(45) Date of Patent: Jun. 4, 2019

(54) APPARATUS AND METHOD FOR AUTOMATICALLY ANALYZING A MOTION IN A SPORT

(71) Applicant: SONY CORPORATION, Tokyo (JP)

(72) Inventors: Hirokazu Hashimoto, Kanagawa (JP); Sho Murakoshi, Tokyo (JP); Hiroshige Okamoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 58 days.

(21) Appl. No.: 15/304,146

(22) PCT Filed: Apr. 14, 2015

(86) PCT No.: PCT/JP2015/002070
§ 371 (c)(1),
(2) Date: Oct. 14, 2016

(87) PCT Pub. No.: WO2015/162871
PCT Pub. Date: Oct. 29, 2015

(65) Prior Publication Data
US 2017/0039882 A1  Feb. 9, 2017

(30) Foreign Application Priority Data

Apr. 22, 2014  (JP) .................. 2014-088030

(51) Int. Cl.
*A63B 69/00* (2006.01)
*A63B 69/36* (2006.01)
*A63B 24/00* (2006.01)
*G09B 19/00* (2006.01)
*A61B 5/11* (2006.01)
(Continued)

(52) U.S. Cl.
CPC ........ *A63B 69/3608* (2013.01); *A61B 5/1127* (2013.01); *A61B 5/7425* (2013.01); *A63B 24/0006* (2013.01); *A63B 71/146* (2013.01); *G09B 19/0038* (2013.01); *A61B 2503/10* (2013.01); *A63B 2024/0012* (2013.01); *A63B 2024/0068* (2013.01); *A63B 2220/803* (2013.01); *A63B 2220/836* (2013.01)

(58) Field of Classification Search
None
See application file for complete search history.

(56) References Cited

U.S. PATENT DOCUMENTS 7,602,301 B1 * 10/2009 Stirling ................ A61B 5/1127
340/573.1
8,460,001 B1 * 6/2013 Chuang .............. G09B 19/0038
434/247

(Continued)

FOREIGN PATENT DOCUMENTS

JP  2012-157644 A  8/2012

*Primary Examiner* — Jason T Yen
(74) *Attorney, Agent, or Firm* — Chip Law Group

(57) ABSTRACT

An apparatus includes a communications interface that receives first sensed data from a first sensor attached to a user and second sensed data from a second sensor attached to a user. That apparatus also includes circuitry that analyzes the first sensed data and the second sensed data and provides a display signal that causes a display to produce first visual information regarding a motion of the user and second visual information regarding the motion of the user, the first visual information being different than the second visual information.

20 Claims, 7 Drawing Sheets

(51) Int. Cl.
*A61B 5/00* (2006.01)
*A63B 71/14* (2006.01)

(56) References Cited

U.S. PATENT DOCUMENTS

| | | | | |
|---|---|---|---|---|
| 2007/0135225 | A1* | 6/2007 | Nieminen | A63B 24/0006 473/212 |
| 2010/0298661 | A1* | 11/2010 | McCombie | G16H 50/50 600/301 |
| 2011/0276153 | A1 | 11/2011 | Selner | |
| 2012/0052972 | A1* | 3/2012 | Bentley | A63B 24/0006 473/223 |
| 2013/0029791 | A1* | 1/2013 | Rose | G09B 19/0038 473/409 |

* cited by examiner

[Fig. 1]
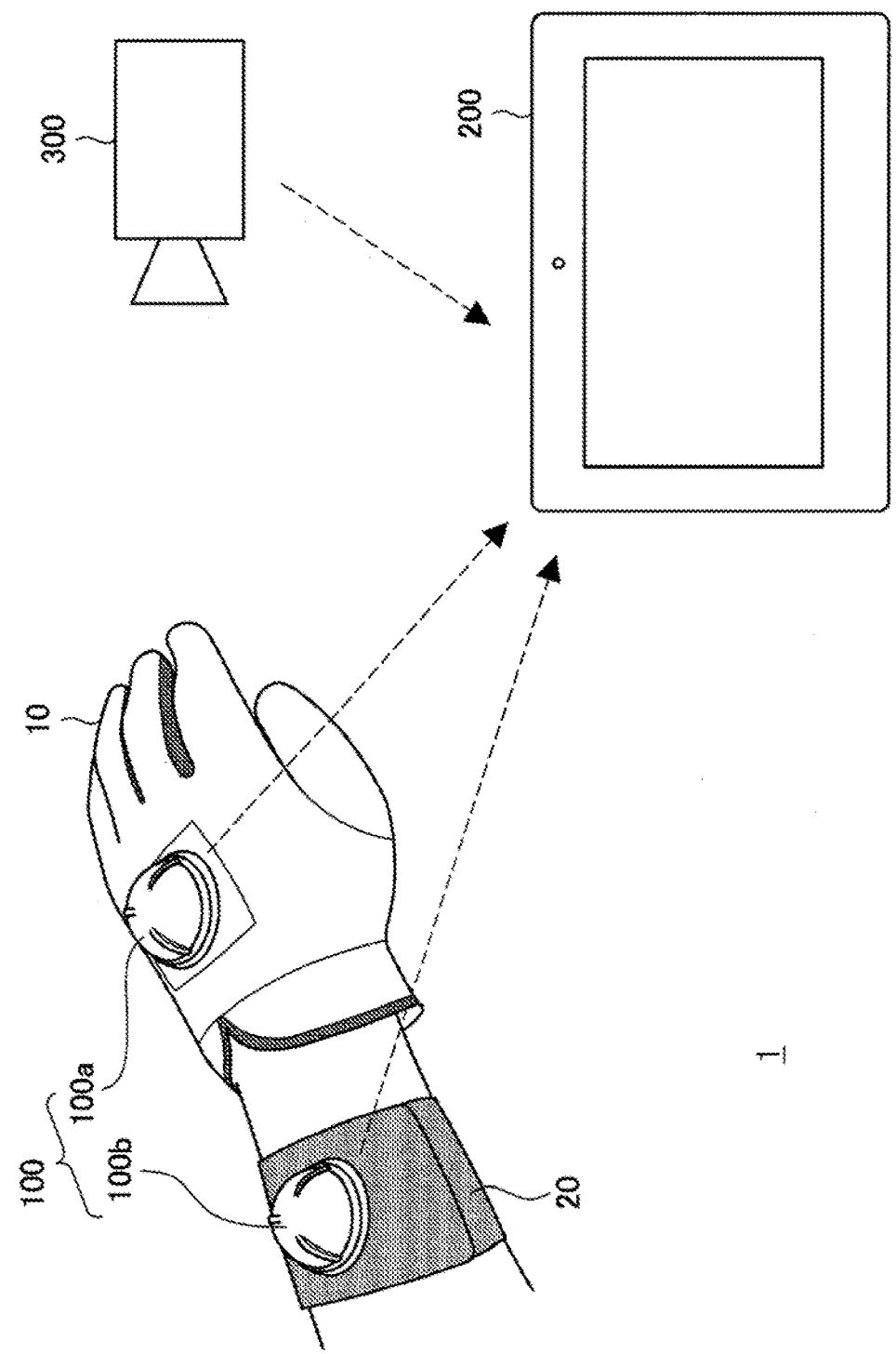

[Fig. 2]
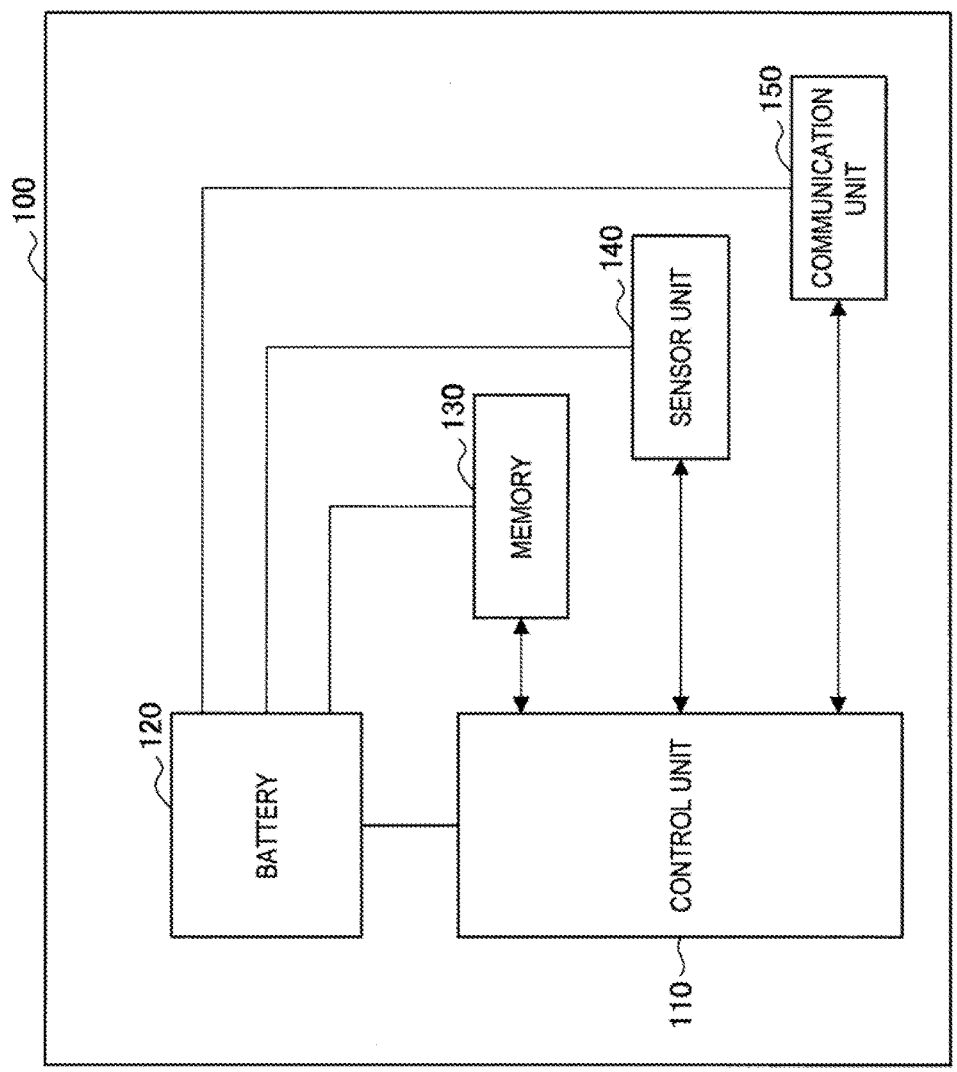

[Fig. 3]
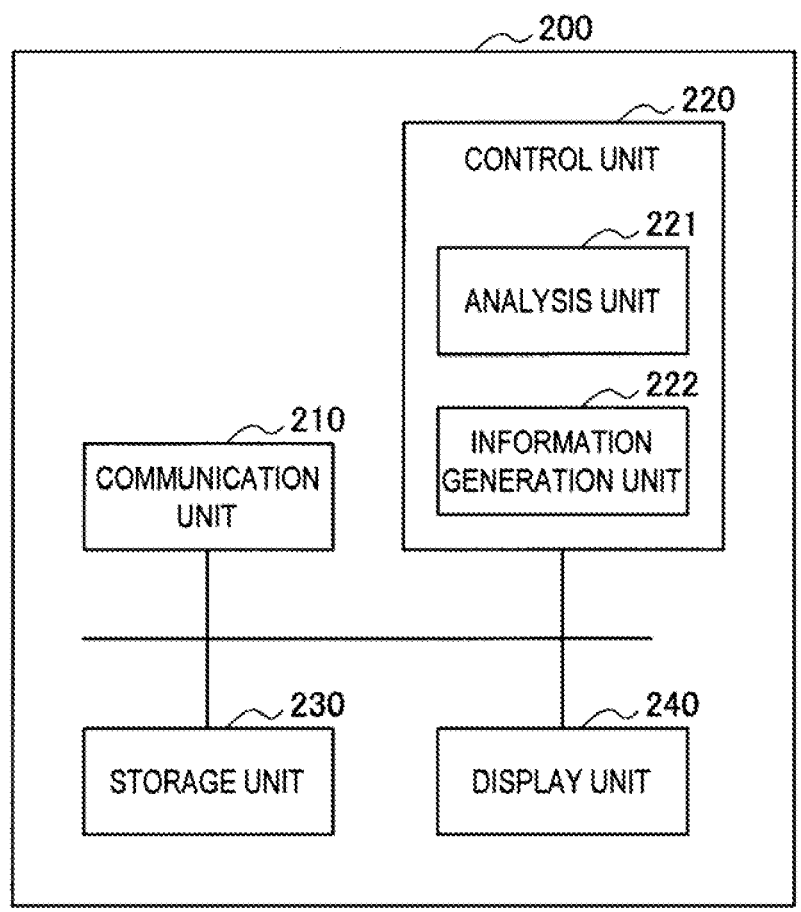

[Fig. 4]
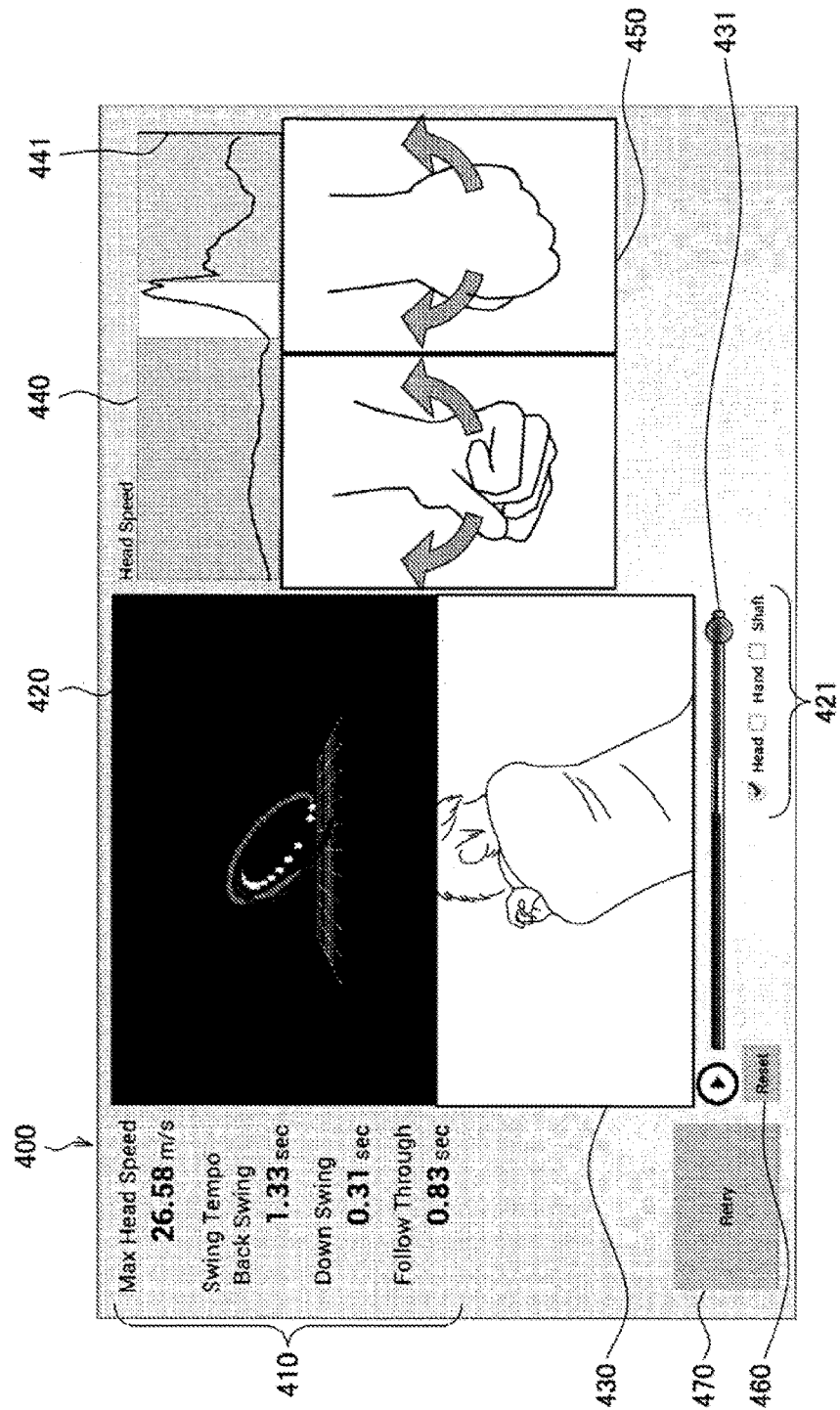

[Fig. 5]
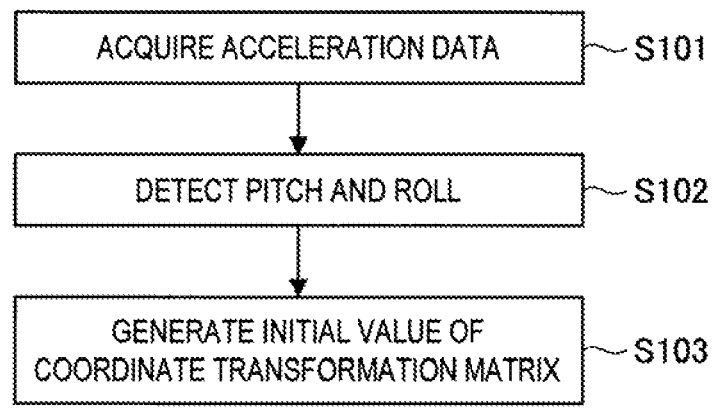

[Fig. 6]
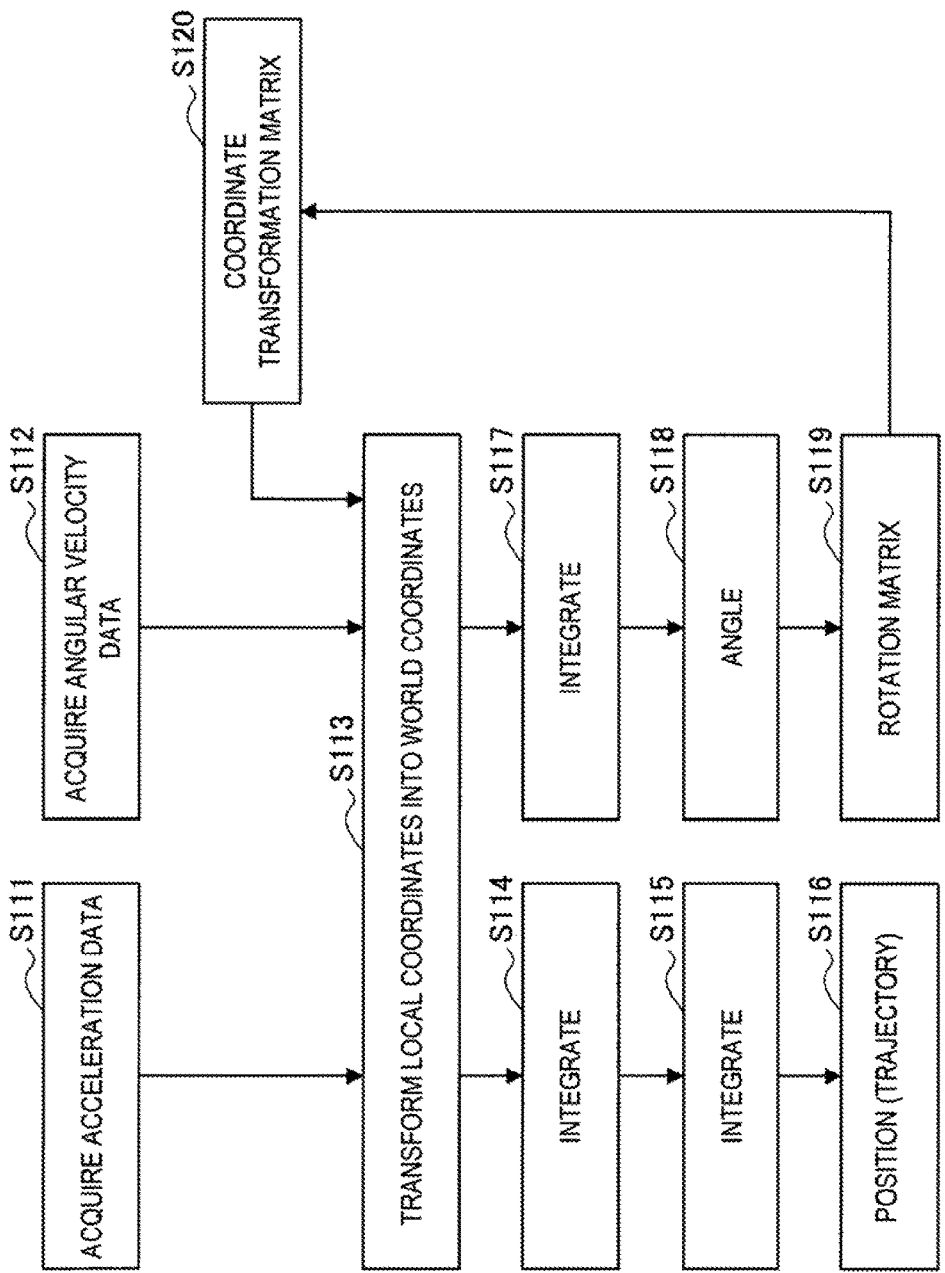

[Fig. 7]
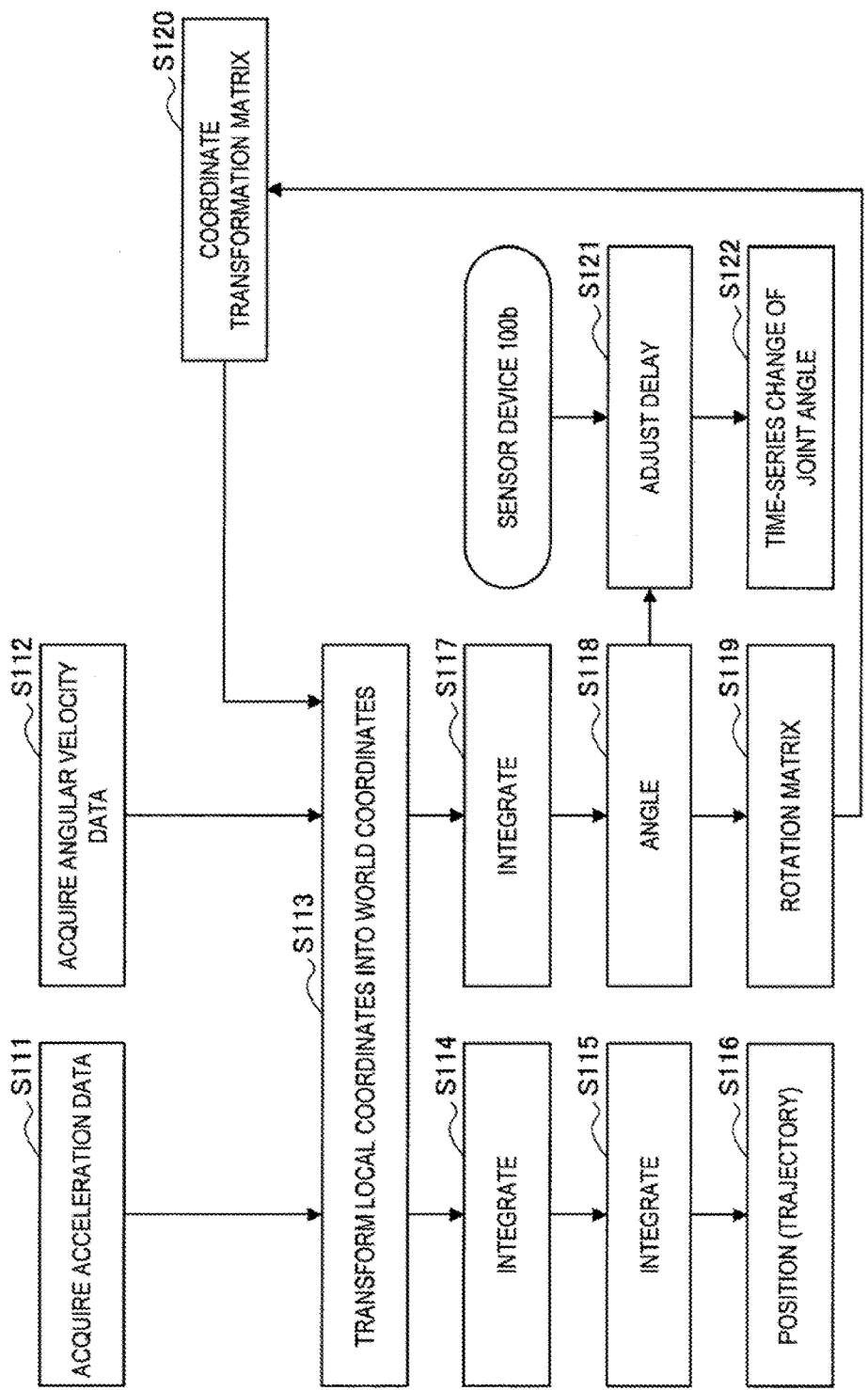

APPARATUS AND METHOD FOR AUTOMATICALLY ANALYZING A MOTION IN A SPORT

CROSS REFERENCE TO RELATED APPLICATIONS

This application is a U.S. National Phase of International Patent Application No. PCT/JP2015/002070 filed on Apr. 14, 2015, which claims priority benefit of Japanese Patent Application No. JP 2014-088030 filed in the Japan Patent Office on Apr. 22, 2014. Each of the above-referenced applications is hereby incorporated herein by reference in its entirety.

This application claims the benefit of Japanese Priority Patent Application JP 2014-088030 filed Apr. 22, 2014, the entire contents of which are incorporated herein by reference.

TECHNICAL FIELD

The present disclosure relates to an information processing apparatus, an information processing method, and a computer program.

BACKGROUND ART

Many technologies for helping a user become proficient in a sport through sensing and analyses have been developed. Among the technologies, statistically analyzing a play of a user and other users is used as one technique. Thus, a technology for automatically analyzing a motion by mounting a sensor device formed by installing sensors such as an acceleration sensor and a gyro sensor on a user or wearable equipment used by the user and analyzing sensed data acquired by the sensors has been proposed (for example, refer to PTL 1).

CITATION LIST

Patent Literature

[PTL 1]
JP 2012-157644A

SUMMARY

Technical Problem

A motion of a player can be visualized when sensed data from a single sensor is used. Thus, if sensed data from a plurality of sensors is used in analysis for analysis and visualization of a motion of a player, the motion of the player can be multi-laterally visualized.

Therefore, the present disclosure proposes a novel and improved information processing apparatus, information processing method, and computer program that can generate information which visualizes a motion of a player multi-laterally using information from a plurality of sensors.

Solution to Problem

Accordingly to one non-limiting aspect, an apparatus is provided that includes a communications interface that receives first sensed data from a first sensor attached to a user and second sensed data from a second sensor attached to a user. That apparatus also includes circuitry that analyzes the first sensed data and the second sensed data and provides a display signal that causes a display to produce first visual information regarding a motion of the user and second visual information regarding the motion of the user, the first visual information being different than the second visual information According to another non-limiting aspect, a method is provided that includes
collecting first sensed data from a first sensor attached to a user and second sensed data from a second sensor attached to a user;
sending via a communications interface the first sensed data and the second sensed data to analysis circuitry; and
receiving from the analysis circuitry a display signal and displaying first visual information regarding a motion of the user and second visual information regarding the motion of the user, the first visual information being different than the second visual information.

According to another non-limiting aspect, an apparatus is provided that includes
a communications interface configured to receive first sensed data from a first sensor attached to a user and a second sensed data from a second sensor attached to a user;
circuitry configured to analyze the first sensed data and the second sensed data and provide a display signal that causes a display to produce first visual information regarding a motion of the user and second visual information regarding the motion of the user, the first visual information being different than the second visual information; and
the display configured to display the first visual information and the second visual information.

Advantageous Effects of Invention

According to an embodiment of the present disclosure described above, a novel and improved information processing apparatus, information processing method, and computer program that can generate information which visualizes a motion of a player multi-laterally using information from a plurality of sensors can be provided.

Note that the effects described above are not necessarily limited, and along with or instead of the effects, any effect that is desired to be introduced in the present specification or other effects that can be expected from the present specification may be exhibited.

BRIEF DESCRIPTION OF DRAWINGS

FIG. 1 is an explanatory diagram showing a configuration example of an information processing system 1 according to an embodiment of the present disclosure.

FIG. 2 is an explanatory diagram showing a functional configuration example of a sensor device 100 according to an embodiment of the present disclosure.

FIG. 3 is an explanatory diagram showing a functional configuration example of an information processing apparatus 200 according to an embodiment of the present disclosure.

FIG. 4 is an explanatory diagram showing an example of information 400 that the information processing apparatus 200 according to an embodiment of the present disclosure causes a display unit 240 to display.

FIG. 5 is a flowchart showing an operation example of the information processing apparatus 200 according to an embodiment of the present disclosure.

FIG. 6 is a flowchart showing an operation example of the information processing apparatus 200 according to an embodiment of the present disclosure.

FIG. 7 is a flowchart showing an operation example of the information processing apparatus 200 according to an embodiment of the present disclosure.

DESCRIPTION OF EMBODIMENTS

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. Embodiment of the present disclosure
1.1. System configuration example
1.2. Functional configuration example
1.3. Information display example
1.4. Analysis process example
2. Conclusion 1. Embodiment of the Present Disclosure 1.1. System Configuration Example First, a configuration example of an information processing system according to an embodiment of the present disclosure will be described with reference to a drawing. FIG. 1 is an explanatory diagram showing the configuration example of the information processing system 1 according to the embodiment of the present disclosure. The information processing system 1 according to the embodiment of the present disclosure shown in FIG. 1 is a system for visualizing and presenting changes in body states of a player playing golf by analyzing motions of the player. Other activities are contemplated as well such as tennis, or bowling where the user moves an object with his arm/wrist/hand along a predetermined trajectory. Hereinbelow, the configuration example of the information processing system 1 according to the embodiment of the present disclosure will be described using FIG. 1.

As shown in FIG. 1, the information processing system 1 according to the embodiment of the present disclosure is configured to include a sensor device 100*a* that is installed on a glove 10 that a player wears on his or her hand when playing golf, a sensor device 100*b* that is installed on a wrist band 20 that the player wraps around his or her wrist when playing golf, an information processing apparatus 200 that visualizes and presents changes in body states of the player using sensed data transmitted from the sensor devices 100*a* and 100*b*, and an imaging device 300 that images a figure of the player playing golf, particularly, a figure of the player swinging a golf club.

The information processing apparatus 200 is an apparatus that processes and displays information, for example, a personal computer, a smartphone (high functional mobile telephone), a tablet-type terminal, or the like. In addition, the sensor devices 100*a* and 100*b* will be referred to simply as a sensor device 100 in description below when it is not necessary to distinguish them from each other.

In the information processing system 1 according to the embodiment of the present disclosure shown in FIG. 1, the respective sensor devices 100*a* and 100*b* transmit sensed data to the information processing apparatus 200, and the information processing apparatus 200 analyzes the sensed data transmitted from the sensor devices 100*a* and 100*b* and presents an analyzed result. The result presented by the information processing apparatus 200 after analyzing the sensed data is a visualized change in a body state of the player playing golf.

Note that, although FIG. 1 illustrates the information processing apparatus 200 and the imaging device 300 as separate devices, the present disclosure is not limited to the example. In other words, the information processing apparatus 200 and the imaging device 300 may be the same device.

As shown in FIG. 1, the sensor device 100*a* is installed on the glove 10, and the sensor device 100*b* is installed on the wrist band 20. Thus, the sensor device 100*a* mainly senses motions of the back portion of the hand of the player, and the sensor device 100*b* mainly senses motions of the wrist portion of the player. In other words, the sensor devices 100*a* and 100*b* are equipped by the user such that the wrist joint of the player is interposed therebetween as shown in FIG. 1.

With the configuration shown in FIG. 1, the information processing system 1 according to the embodiment of the present disclosure can cause the information processing apparatus 200 to analyze the sensed data obtained by the sensor devices 100*a* and 100*b* and to visualize and present information regarding a change in a body state of the player playing golf and a swing of a golf club. In addition, by causing the wearable equipment that is provided with the plurality of sensor devices 100*a* and 100*b* to be mounted on the player such that the joint, for example, the wrist joint, is interposed between the devices, the information processing system 1 according to the embodiment of the present disclosure can obtain a change in a body state of the player that would otherwise be difficult to obtain with a single sensor device, for example, a time-series change in angles of the wrist of the player when, for example, swinging a golf club, and the like can be obtained.

Although the present embodiment shows the case in which the sensor device 100*a* is installed on the glove 10 and the sensor device 100*b* is installed on the wrist band 20, the present disclosure is not limited to the example. The sensor device 100 that obtains the sensed data can be mounted in various positions of the head, shoulders, waist, knees, and the like of the player in which a change in a body state of the player can be obtained.

The configuration example of the information processing system 1 according to the embodiment of the present disclosure has been described above using FIG. 1. Next, functional configuration examples of the respective devices constituting the information processing system 1 according to an embodiment of the present disclosure will be described.

1.2. Functional Configuration Example

First, a functional configuration example of the sensor device 100 according to an embodiment of the present disclosure will be described. FIG. 2 is an explanatory diagram showing the functional configuration example of the sensor device 100 according to the embodiment of the present disclosure. Hereinbelow, the functional configuration example of the sensor device 100 according to the embodiment of the present disclosure will be described using FIG. 2.

As shown in FIG. 2, the sensor device 100 according to the embodiment of the present disclosure is configured to include a control unit 110, a battery 120, a memory 130, a sensor unit 140, and a communication unit 150.

The control unit 110 controls operations of the sensor device 100, and can be configured by, for example, a central processing unit (CPU), or the like. When the control unit 110 is configured by a CPU, the CPU can be configured by an electronic circuit.

The battery 120 is a battery for supplying power to the control unit 110, the memory 130, the sensor unit 140, and the communication unit 150. Note that the type of the battery 120 may be a secondary battery that can be charged repeatedly, or a primary battery that only can discharge.

The memory 130 stores various kinds of information, particularly information obtained by the sensor unit 140. The control unit 110, for example, causes the memory 130 to store information. In addition, the information stored in the memory 130 is, for example, read by the control unit 110 and transmitted by the communication unit 150. The memory 130 is configured to be capable of retaining information even without supply of power from the battery 120; however, power is supplied from the battery 120 when information is written onto the memory 130 and when information is read from the memory 130. In addition, the memory 130 may store computer programs read and sequentially executed by the control unit 110.

The sensor unit 140 is constituted by sensors that acquire directions and attitudes of hitting equipment or wearable equipment on which the sensor device 100 is installed, impacts exerted on the wearable equipment, and other states thereof. In the present embodiment, the sensor unit 140 acquires impacts exerted on the glove 10 and wrist band 20 both having the sensor device 100 installed thereon and other states thereof. The sensor unit 140 operates by receiving supply of power from the battery 120. The sensors constituting the sensor unit 140 include, for example, an acceleration sensor with a single axis, three axes, six axes, nine axes, or the like, a gyro sensor (angular velocity), a geomagnetic sensor, and the like.

The sensor unit 140 may also include, for example, a shock sensor, and a motion sensor. The shock sensor is a sensor that detects impacts transmitted by the sensor device 100 from the user or the hitting equipment or wearable equipment, and can include, for example, an acceleration sensor with a single axis in the present embodiment. The motion sensor is a sensor that detects behaviors of the sensor device 100 with, for example, higher resolving power than the shock sensor, and can include, for example, acceleration sensors with three axes, six axes, and nine axes, a gyro sensor, a geomagnetic sensor, and the like in the present embodiment. The sensors can be realized using, for example, a piezo-resistance-type or capacitance-type acceleration sensor, and the like.

The sensor unit 140 may include all kinds of sensors for acquiring states of the hitting equipment and wearable equipment both having the sensor device 100 installed thereon, for example, a temperature sensor, a pressure sensor, a Global Positioning System (GPS) receiver, and the like, in addition to the above-described shock sensor and motion sensor.

The communication unit 150 transmits information to an external device, for example, the information processing apparatus 200. As information to be transmitted to the information processing apparatus 200, the communication unit 150 transmits information that, for example, is acquired by the sensor unit 140 with respect to the hitting equipment and wearable equipment both having the sensor device 100 installed thereon. The communication unit 150 transmits information using, for example, Bluetooth (a registered trademark), a wireless local area network (LAN), or the like. Note that, since the information acquired by the sensor unit 140 does not have to be transmitted to the information processing apparatus 200 in real time, the communication unit 150 may transmit information to the information processing apparatus 200 through, for example, wired communication using a USB cable, a LAN cable, or the like after plays are finished.

The sensor unit 140 is illustrated as one block in FIG. 2, but when the sensor unit 140 is constituted by the motion sensor and the shock sensor as described above, for example, the battery 120 may supply power separately to the respective motion sensor and the shock sensor. In this case, the sensor device 100 can be separately provided with a switch for controlling power supply to the motion sensor and a switch for controlling power supply to the shock sensor. The control unit 110 can control operations of the switches such that power supply to any one of the motion sensor and the shock sensor is stopped.

The functional configuration example of the sensor device 100 according to the embodiment of the present disclosure has been described above using FIG. 2. Next, the functional configuration example of the information processing apparatus 200 according to the embodiment of the present disclosure will be described.

FIG. 3 is an explanatory diagram showing the functional configuration example of the information processing apparatus 200 according to the embodiment of the present disclosure. Hereinbelow, the functional configuration example of the information processing apparatus 200 according to the embodiment of the present disclosure will be described using FIG. 3.

As shown in FIG. 3, the information processing apparatus 200 according to the embodiment of the present disclosure is configured to include a communication unit 210, a control unit 220, a storage unit 230, and a display unit 240.

The communication unit 210 executes communication with other devices. The communication unit 210 executes communication with other devices using, for example, Bluetooth (a registered trademark), a wireless LAN, or the like. In the present embodiment, the communication unit 210 receives sensed data transmitted from the sensor device 100. Then, the communication unit 210 can supply the sensed data received from the sensor device 100 to the control unit 220 and the storage unit 230.

The control unit 220 controls operations of the information processing apparatus 200. The control unit 220 can be configured by, for example, a CPU or the like. When the control unit 220 is configured by a CPU, the CPU can be configured by an electronic circuit. In the present embodiment, the control unit 220 executes a process of analyzing a motion of the player playing golf using the sensed data received by the communication unit 210 from the sensor device 100. Further, in the present embodiment, the control unit 220 executes a process of presenting a result of the analysis of the motion of the player playing golf on the display unit 240.

The control unit 220 computes absolute positions of the sensor devices 100*a* and 100*b*, and an absolute position of the head of a golf club that can be estimated from the absolute positions of the sensor devices 100*a* and 100*b* using the sensed data of the acceleration sensor. In addition, the control unit 220 successively computes a rotation matrix using sensed data of the angular velocity sensor. By successively computing the rotation matrix using the sensed data of the angular velocity sensor, the control unit 220 generates a coordinate transformation matrix from the rotation matrix, and then by transforming local coordinates of the sensor devices 100a and 100b into world coordinates using the coordinate transformation matrix, it is possible to know acceleration of the sensor devices 100a and 100b in the world coordinate system. By integrating the acceleration of the sensor devices 100a and 100b in the world coordinate system two times, the control unit 220 can obtain a trajectory of the sensor devices 100a and 100b.

Then, the control unit 220 acquires pieces of angle information of the respective sensor devices 100a and 100b from the sensed data from the two sensor devices 100a and 100b. Then, the control unit 220 obtains the difference between the pieces of angle information of the sensor devices 100a and 100b, and thereby acquires a time-series change of the wrist joint of the player. By analyzing the sensed data from the plurality of sensor devices 100a and 100b worn by the player, the control unit 220 can obtain information of a change in a body state of the player that would otherwise be difficult to obtain with a single sensor device, for example, a time-series change of a wrist angle or the like, and present the change in the body state of the player.

The control unit 220 can be configured to include an analysis unit 221 and an information generation unit 222. The analysis unit 221 analyzes sensed data detected by the two respective sensor devices 100a and 100b with which the player is equipped. The information generation unit 222 generates information that visualizes the figure of a change in a body state of the player based on an analysis result of the sensed data by the analysis unit 221. The information generated by the information generation unit 222 is transmitted to the display unit 240, and thereby the information processing apparatus 200 can present the information based on the sensed data detected by the respective sensor devices 100a and 100b. An example of an analysis process using the sensed data by the analysis unit 221 will be described later in detail.

The storage unit 230 retains various kinds of information, particularly information used in processes in the control unit 220. The storage unit 230 can be configured by, for example, a ROM, a RAM, a hard disk drive (HDD), a solid-state drive (SSD), and the like. The control unit 220, for example, causes the storage unit 230 to store information. In addition, the information retained in the storage unit 230 is read by, for example, the control unit 220. Further, the storage unit 230 may retain computer programs read and sequentially executed by the control unit 220.

The display unit 240 displays various kinds of information, particularly, information generated as a result of processes of the control unit 220. The display unit 240 can be configured as a display device, for example, a liquid crystal display, an organic EL display, or the like. In the present embodiment, the display unit 240 displays a result obtained by analyzing a motion of the player playing golf which is obtained from analysis of the sensed data in the control unit 220. An example of the result of analysis displayed by the display unit 240 will be described later. The display unit 240 may be provided with a touch panel, and a user can manipulate the information processing apparatus 200 by touching the display unit 240 with his or her finger or bringing his or her finger or the like close thereto.

Although FIG. 3 illustrates that the information processing apparatus 200 includes the display unit 240, the present disclosure is not limited thereto. The display unit 240 may be configured as a separate device from the information processing apparatus 200. In addition, the information processing apparatus 200 may include the imaging device 300 shown in the system configuration example of FIG. 1.

With the configuration shown in FIG. 3, the information processing apparatus 200 according to the embodiment of the present disclosure can analyze sensed data obtained by the sensor devices 100a and 100b and visualize and present a change in a body state of a player playing golf. In addition, by analyzing sensed data from the plurality of sensor devices 100a and 100b mounted on a player, the information processing apparatus 200 according to the embodiment of the present disclosure can obtain a change in a body state of the player that would otherwise be difficult to obtain with a single sensor device, for example, a time-series change in an angle of a wrist of the player when swinging a golf club, and thereby can present the change in the body state of the player.

The functional configuration example of the information processing apparatus 200 according to the embodiment of the present disclosure has been described above using FIG. 3. Next, an example of information displayed by the information processing apparatus 200 according to an embodiment of the present disclosure will be described.

1.3. Information Display Example

FIG. 4 is an explanatory diagram showing an example of information 400 that the information processing apparatus 200 according to an embodiment of the present disclosure causes the display unit 240 to display. The information 400 shown in FIG. 4 includes various kinds of information obtained through analysis of sensed data transmitted from the sensor device 100 and a dynamic image captured by the imaging device 300. Note that the information 400 shown in FIG. 4 can be generated by the information generation unit 222.

The information 400 shown in FIG. 4 includes swing information 410 indicating a speed of the head of a golf club which a player swings and a tempo of the swing of the golf club, trajectory information 420 indicating a trajectory of the swing of the golf club using three-dimensional modeling, dynamic image information 430 indicating a dynamic image of the player captured by the imaging device 300, graph information 440 indicating a change in the speed of the head of the golf club in a graph, wrist information 450 indicating a change in a state of a wrist of the player during the swing in an animation, a reset button 460 for causing display of a trajectory displayed in the trajectory information 420 to return to an initial state, and a retry button 470 for acquiring sensed data again and for executing analysis again.

The swing information 410 includes the maximum value of the speed of the golf club head, a backswing time taken from an address posture and pulling back of the club to take an end-backswing position, a downswing time taken from the end-backswing position to contact, and a follow-through time taken from contact and continuation of a series of motions to a finishing posture.

A trajectory displayed in the trajectory information 420 can be rotated in an arbitrary direction and displayed according to user manipulations. Note that display of a trajectory displayed in the trajectory information 420 returns to an initial state when a user touches the reset button 460. The trajectory displayed in the trajectory information 420 can be changed according to a selection manipulation by the user with respect to a check box 421. As a trajectory displayed in the trajectory information 420 in the present embodiment, a position of the golf club head estimated from a position of the sensor device 100, a position of the sensor device 100, and a position of the shaft of the golf club estimated from the position of the sensor device 100 can be selected.

In addition, the information processing apparatus 200 can reproduce a dynamic image displayed in the dynamic image information 430 from a position designated in a user manipulation performed with respect to a slider bar 431.

As shown in FIG. 4, the information processing apparatus 200 may display the trajectory displayed in the trajectory information 420, the slider bar 431, and the background color of the graph information 440 in different colors for the backswing time, the downswing time, and the follow-through time.

The pieces of information included in the information 400 shown in FIG. 4 are based on the sensed data transmitted from the sensor devices 100*a* and 100*b* and the dynamic image captured by the imaging device 300. The swing information 410, the trajectory information 420, and the graph information 440 can be generated based on sensed data transmitted from a single sensor device 100 (for example, the sensor device 100*a*).

The pieces of information included in the information 400 shown in FIG. 4 can be generated through arithmetic processing performed by the control unit 220 with respect to sensed data and image processing performed on the dynamic image captured by the imaging device 300. Particularly, the wrist information 450 can be generated from a time-series change in an angle of the wrist of the player during the swing obtained as the control unit 220 analyzes the sensed data from the sensor devices 100*a* and 100*b* and then the difference between pieces of angle information of the sensor devices 100*a* and 100*b* is taken.

When the user instructs reproduction of the dynamic image displayed as the dynamic image information 430 to the information processing apparatus 200 through, for example, a predetermined manipulation, the information processing apparatus 200 not only outputs the dynamic image displayed as the dynamic image information 430 to the display unit 240 but also outputs other information, for example, a change in a state of the wrist of the player displayed as the wrist information 450 to the display unit 240 in synchronization with the dynamic image displayed as the dynamic image information 430. In addition, while the dynamic image displayed as the dynamic image information 430 is reproduced, a bar 441 of the graph information 440 moves in synchronization with the reproduction of the dynamic image.

By generating information for visualizing the motion of the player that serves as a foundation for the information 400 as shown in FIG. 4, the information processing apparatus 200 can present, for example, the trajectory of the hand holding the golf club during swing, and the motion of the joint during swing, particularly of the wrist of the hand holding the golf club. If the player views the information 400 as shown in FIG. 4, he or she can ascertain whether the trajectory of the swing is close to inside-out that is an ideal swing or outside-in that is not an ideal swing.

When playing golf, if the wrist turns at the time of impact during swing, the speed of the head increases. If the player views the information 400 as shown in FIG. 4, he or she can ascertain whether or not his or her wrist turns earlier than the time of impact during swing.

The example of the information that the information processing apparatus 200 displays according to the embodiment of the present disclosure has been described above using FIG. 4. Of course, it is needless to say that information displayed through the analysis processing performed with respect to sensed data transmitted from the sensor devices 100*a* and 100*b* and the image processing performed with respect to a dynamic image captured by the imaging device 300 is not limited to that shown in FIG. 4.

By presenting the information 400 as shown in FIG. 4, the information processing apparatus 200 according to an embodiment of the present disclosure can present a change in a body state of a player and information that visualizes a state of equipment (a golf club) that the player uses to the player. Viewing the information 400 that the information processing apparatus 200 presents can help the player become proficient in his or her playing techniques. In addition, viewing the information 400 that the information processing apparatus 200 can help a coach who trains the player train the player better.

1.4. Analysis Process Example

Next, an analysis process example of sensed data performed by the information processing apparatus 200 according to an embodiment of the present disclosure will be described. FIGS. 5 to 7 are flowcharts showing operation examples of the information processing apparatus 200 according to the embodiment of the present disclosure. The flowcharts shown in FIGS. 5 to 7 are for the analysis process examples of sensed data performed by the information processing apparatus 200 according to the embodiment of the present disclosure. Note that a series of all processes described hereinbelow can be executed by the analysis unit 221. Hereinbelow, the operation examples of the information processing apparatus 200 according to the embodiment of the present disclosure will be described using FIGS. 5 to 7.

FIG. 5 shows the analysis process example of sensed data transmitted from the sensor device 100*a* performed by the information processing apparatus 200 before a player swings a golf club. Before the player swings the golf club, the acceleration sensor included in the sensor unit 140 is assumed to stand still, and when a direction of gravitational acceleration is detected, pitch and roll of the sensor device 100*a* are ascertained. Thus, the information processing apparatus 200 acquires acceleration data from the sensor device 100*a* (Step S101), detects the direction of gravitational acceleration from the acceleration data, and thereby detects pitch and roll of the sensor device 100*a* (Step S102).

In order to obtain a trajectory of a swing of a player, it is necessary for the information processing apparatus 200 to ascertain world coordinates of the sensor device 100*a*. When the pitch and roll of the sensor device 100*a* are ascertained, a transformation matrix for transforming local coordinates of the sensor device 100*a* into the world coordinates can be generated. Thus, using the pitch and roll of the sensor device 100*a* detected in Step S102, the information processing apparatus 200 generates initial values of a coordinate transformation matrix for transforming local coordinates of the sensor device 100*a* into the world coordinates (Step S103). By generating the coordinate transformation matrix, the information processing apparatus 200 can generate the world coordinates of the sensor device 100*a* using the sensed data transmitted from the sensor device 100*a*.

FIG. 6 shows the analysis process example of the sensed data transmitted from the sensor device 100*a* performed by the information processing apparatus 200 when the player swings the golf club. When the player swings the golf club, the information processing apparatus 200 acquires acceleration data and angular velocity data from the sensor device 100a (Steps S111 and S112), and transforms the local coordinates of the sensor device 100a into the world coordinates using the coordinate transformation matrix obtained in the process shown in FIG. 5 (Step S113).

When the acceleration is integrated two times, the position of the sensor device is obtained. Thus, when the local coordinates of the sensor device 100a are transformed into the world coordinates in Step S113, the information processing apparatus 200 integrates the acceleration data after the transformation two times (Steps S114 and S115), and then computes the position (trajectory) of the sensor device 100a (Step S116). Further, the information processing apparatus 200 integrates the angular velocity data after the transformation (Step S117), computes an angle (Step S118), and then updates a rotation matrix (Step S119).

The information processing apparatus 200 integrates angular velocities each time sensed data is acquired from the sensor device 100a to compute angles, adds the angles, and thereby updates the rotation matrix. Then, the information processing apparatus 200 computes the coordinate transformation matrix from the updated rotation matrix (Step S120). The coordinate transformation matrix computed in Step S120 is used in the transformation process in Step S113 to transform the local coordinates of the sensor device 100a into the world coordinates.

FIG. 7 shows the analysis process example of sensed data transmitted from the sensor devices 100a and 100b performed by the information processing apparatus 200 when the player swings the golf club. By analyzing the sensed data transmitted from the two sensor devices 100a and 100b, the information processing apparatus 200 can generate data that serves as a foundation for the wrist information 450 shown in FIG. 4.

When pieces of the sensed data transmitted from the two sensor devices 100a and 100b are used, the pieces of sensed data do not arrive from the sensor devices 100a and 100b at completely the same time at all times, and thus the information processing apparatus 200 adjusts a delay of the pieces of sensed data transmitted from the sensor devices 100a and 100b (Step S121). The adjustment of a delay of Step S121 is not limited to a specific method. An example of the adjustment of a delay for sensed data will be described below.

The information processing apparatus 200 may adjust a delay based on time stamps issued to the pieces of sensed data transmitted from the respective sensor devices 100a and 100b. In addition, since the sensor devices 100a and 100b are respectively mounted on the back of a hand and near the wrist thereof, there is a high possibility of the sensed data changing in the same way. Thus, the information processing apparatus 200 may adjust a delay by causing one piece of sensed data to match the other piece of sensed data so that the sensed data change in the same way. Of course, it is needless to say that a delay adjustment process for sensed data is not limited to these two examples.

Then, when the delay has been adjusted in Step S121, the information processing apparatus 200 successively computes a time-series change of angles (joint angles) of a joint (of the wrist in the present embodiment) using the sensed data transmitted from the sensor devices 100a and 100b (Step S122). To be specific, after adjusting the delay, the information processing apparatus 200 obtains the difference between pieces of angle information of the sensor devices 100a and 100b, and then acquires the time-series change of the joint of the wrist of the player.

By executing the series of operations described above, the information processing apparatus 200 according to the embodiment of the present disclosure can analyze the sensed data transmitted from the sensor devices 100a and 100b and generate various types of information that serve as a foundation of the information 400 as shown in FIG. 4. Thus, by executing the series of operations described above, the information processing apparatus 200 according to the embodiment of the present disclosure can generate information that visualizes the change in the body state of the player.

By analyzing the sensed data transmitted from the sensor devices 100a and 100b, the information processing apparatus 200 according to the embodiment of the present disclosure can obtain not only the information that visualizes the change in the body state of the player but also information relating to his or her play of golf. The information processing apparatus 200 may decide a time at which a value of the acceleration sensor exceeds a predetermined threshold value, for example, as an impact time at which the golf club hits a golf ball.

The information processing apparatus 200 may also set, for example, a time from when the sensor devices 100a and 100b stand still and values of sensed data start changing to when directions of the sensor devices 100a and 100b radically change in their moving states as a back-swing time, a time from when the directions of the sensor devices 100a and 100b radically change in their moving states to the impact time as a down-swing time, and a time from the impact time to when the sensor devices 100a and 100b stand still as a follow-through time. The back-swing time, the down-swing time, and the follow-through time decided in this manner can be displayed on the display unit 240 as the swing information 410 of the information 400 shown in FIG. 4.

2. Conclusion

According to the embodiments of the present disclosure described above, the information processing system 1 in which the information processing apparatus 200 analyzes sensed data that the sensor devices 100a and 100b obtain is provided. In the information processing system 1 according to the embodiments, as the information processing apparatus 200 analyzes the sensed data, a change in a body state of a player playing golf can be visualized and presented.

In addition, when a player is equipped with the wearable equipment on which the plurality of sensor devices 100a and 100b are installed to play golf, the information processing system 1 according to the embodiments of the present disclosure can obtain a change in a body state of the player, for example, a time-series change in angles of a wrist of the player while he or she swings a golf club that would otherwise be difficult to obtain with a single sensor device, and then can generate information that visualizes the change in the body state of the player and a state of equipment (the golf club) that the player uses. Thereby, viewing of information that the information processing apparatus 200 can help the player become proficient in his or her play.

In the embodiments described above, the case in which the sensor device 100a is installed on the glove 10 and the sensor device 100b is installed on the wrist band 20 is shown. By installing the sensor device 100a on the glove 10 and the sensor device 100b on the wrist band 20, the information processing system 1 according to the embodiments of the present disclosure can visualize motions of the joint of a wrist of the player wearing the glove 10 and the wrist band 20 using only the two sensor devices 100a and 100b. In other words, the information processing system 1 according to the embodiments of the present disclosure can present information that can contribute to proficiency in play of the player with a minimum number of sensor devices.

Although the case in which the sensor device 100a is installed on the glove 10 and the sensor device 100b is installed on the wrist band 20 is shown in the embodiments described above, the present disclosure is not limited thereto. As described above, the sensor device 100 that obtains sensed data can be installed in various positions of the head, shoulders, waist, knees, and the like of the player in which a change in a body state of the player can be obtained. For example, by mounting one near a wrist of the player and the other near the waist, the information processing system 1 can generate information that visualizes motions of the waist of the player during a swing and then visualize and present the motions of the waist of the player.

Steps in processes executed by devices in this specification are not necessarily executed chronologically in the order described in a sequence chart or a flow chart. For example, steps in processes executed by devices may be executed in a different order from the order described in a flow chart or may be executed in parallel.

Further, a computer program can be created which causes hardware such as a CPU, ROM, or RAM, incorporated in each of the devices, to function in a manner similar to that of structures in the above-described devices. Furthermore, it is possible to provide a recording medium having the computer program recorded thereon. Moreover, by configuring respective functional blocks shown in a functional block diagram as hardware, the hardware can achieve a series of processes.

Furthermore, the information processing apparatus 200 according to the embodiments of the present disclosure may be realized as a separate device from a device provided with a display on which images are displayed as results of processes of the information processing apparatus 200 (for example, a server device connected to a device provided with a display via a network such as the Internet), or may be realized as a terminal device that receives information from a server device. In addition, a configuration of the information processing apparatus 200 according to the embodiments of the present disclosure may be realized by a single device, or may be realized by a system in which a plurality of devices are linked to each other. In such a system in which a plurality of devices are linked to each other, for example, a combination of a plurality of server devices, a combination of a server device and a terminal device, or the like can be included.

Note that software that realizes a user interface or an application shown in the above-described embodiments may be realized as a web application that is used via a network such as the Internet. Such a web application may be realized with a markup language, for example, HyperText Markup Language (HTML), Standard Generalized Markup Language (SGML), Extensible Markup Language (XML), or the like.

It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative and demonstrative, and not limitative. In other words, the technology according to the present disclosure can exhibit other effects that are evident to those skilled in the art along with or instead of the effects based on the present specification.

(1) According to one embodiment, an apparatus according to the embodiment includes a communications interface configured to receive first sensed data from a first sensor attached to a user and second sensed data from a second sensor attached to a user; and circuitry configured to analyze the first sensed data and the second sensed data and provide a display signal that causes a display to produce first visual information regarding a motion of the user and second visual information regarding the motion of the user, the first visual information being different than the second visual information.

(2) An aspect of the apparatus of (1) is that wherein the first visual information includes analysis data of the motion of the user.

(3) An aspect of the apparatus of (1) and/or (2) is that wherein the first visual information includes a trajectory of an object swung by the user as part of the motion of the user.

(4) An aspect of the apparatus of (1) through (3) is that wherein the first visual information includes a change in state of a body part of the user.

(5) An aspect of the apparatus of (1) through (4) is that wherein the circuitry is configured to cause the display to provide a user selectable indication that identifies a selected body part that is associated with the change in the state, and in response to a selection of the user selectable indication, the circuitry analyzes the motion of the selected body part and includes in the display signal the first visual information regarding the change in state of the selected body part.

(6) An aspect of the apparatus of (1) through (3) is that wherein the circuitry is configured to cause the display to provide a user selectable indication to reset a displayed trajectory of the object swung by the user so that another motion event can be captured, analyzed and displayed.

(7) An aspect of the apparatus of (1) through (6) is that wherein the first visualization information includes at least one of an image, a figure, a video and a picture.

(8) An aspect of the apparatus of (1) through (7) is that wherein the first visual information and the second visual information are displayed in a synchronous relationship so as to show a time-based relationship between the first visual information and the second visual information.

(9) An aspect of the apparatus of (1) through (8) is that wherein the first visual information relates to an object trajectory and the second visual information relates to a hand and/or wrist change of state of a user.

(10) An aspect of the apparatus of (1) through (9) is that wherein the object trajectory is a trajectory of a golf club or a tennis racket.

(11) According to a method embodiment, the method includes collecting first sensed data from a first sensor attached to a user and second sensed data from a second sensor attached to a user;

sending via a communications interface the first sensed data and the second sensed data to analysis circuitry; and receiving from the analysis circuitry a display signal and displaying first visual information regarding a motion of the user and second visual information regarding the motion of the user, the first visual information being different than the second visual information.

(12) An aspect of the method of (11) is that wherein the first visual information includes analysis data of the motion of the user.

(13) An aspect of the method of (11) and/or (12) is that wherein
the first visual information includes a trajectory of an object swung by the user as part of the motion of the user.

(14) An aspect of the method of (11) through (13) is that wherein
the first visual information includes a change in state of a body part of the user.

(15) An aspect of the method of (11) through (14) is that wherein
the displaying includes displaying a user selectable indication that identifies a selected body part that is associated with the change in the state, and in response to a selection of the user selectable indication, the displaying includes displaying the first visual information regarding the change in state of the selected body part.

(16) An aspect of the method of (13) through (15) is that wherein
the displaying includes displaying a user selectable indication to reset a displayed trajectory of the object swung by the user so that another motion event can be captured, analyzed and displayed.

(17) An aspect of the method of (11) through (16) is that wherein the first visualization information includes at least one of an image, a figure, a video and a picture.

(18) An aspect of the method of (11) through (17) is that wherein the displaying includes displaying the first visual information and the second visual information in a synchronous relationship so as to show a time-based relationship between the first visual information and the second visual information.

(19) According to another apparatus embodiment, the apparatus includes
a communications interface configured to receive first sensed data from a first sensor attached to a user and a second sensed data from a second sensor attached to a user;
circuitry configured to analyze the first sensed data and the second sensed data and provide a display signal that causes a display to produce first visual information regarding a motion of the user and second visual information regarding the motion of the user, the first visual information being different than the second visual information; and
the display configured to display the first visual information and the second visual information.

(20) An aspect of the apparatus of (19) is that wherein the first visual information includes analysis data of the motion of the user.

(21) An information processing apparatus including:
an analysis unit configured to analyze sensed data detected by a respective plurality of sensor devices that are mounted on a player; and
an information generation unit configured to generate information that visualizes a figure of a change in a body state of the player on which the plurality of sensor devices are mounted based on an analysis result of the analysis unit.

(22) The information processing apparatus according to (21), wherein the plurality of sensor devices are installed at positions at which a joint of the player is interposed between the plurality of sensor devices.

(23) The information processing apparatus according to (22),
wherein the joint of the player is a wrist of the player, and
wherein the information generation unit generates information that visualizes a figure of a change in the wrist of the player based on an analysis result of the analysis unit.

(24) The information processing apparatus according to any of (21) to (23), wherein the information generation unit generates information relating to a swing of a golf club performed by the player.

(25) An information processing method including:
analyzing sensed data detected by a respective plurality of sensor devices that are mounted on a player; and
generating information that visualizes a figure of a change in a body state of the player on which the plurality of sensor devices are mounted based on a result of the analysis.

(26) A computer program causing a computer to execute:
analyzing sensed data detected by a respective plurality of sensor devices that are mounted on a player; and
generating information that visualizes a figure of a change in a body state of the player on which the plurality of sensor devices are mounted based on a result of the analysis.

REFERENCE SIGNS LIST 1 information processing system
10 glove
20 wrist band
100, 100a, 100b sensor device
110 control unit
120 battery
130 memory
140 sensor unit
150 communication unit
200 information processing apparatus
210 communication unit
220 control unit
221 analysis unit
222 information generation unit
230 storage unit
240 display unit
300 imaging device

The invention claimed is:
1. An apparatus, comprising:
circuitry configured to:
receive first data from a first sensor attached to a first body part of a user, and second data from a second sensor attached to a second body part of the user;
adjust a delay of at least one of the first data or the second data for analysis of a body movement of the user, wherein the adjustment is based on a time stamp issued to each of the first data and the second data;
determine a time-series change of angles of the first body part to represent the body movement, based on the first data, the second data, and the adjusted delay; and
generate a display signal that causes a display device to generate first visual information regarding the time-series change of the angles, and second visual information regarding the body movement so as to visualize the body movement, wherein the generation of the display signal is based on at least one of the first data or the second data, and wherein the first visual information is different from the second visual information.

2. The apparatus of claim 1, wherein the first visual information is based on analysis of the body movement of the user.

3. The apparatus of claim 1, wherein the first visual information includes a trajectory, of an object based on a user swing, as part of the body movement of the user.

4. The apparatus of claim 1, wherein the first visual information includes a change in a state of at least one of the first body part or the second body part.

5. The apparatus of claim 4, wherein the circuitry is further configured to:
cause the display device to provide a user selectable indication that identifies a selected body part associated with the change in the state;
analyze the body movement of the selected body part, based on a selection of the user selectable indication; and
include in the display signal the first visual information based on the change in the state of the selected body part.

6. The apparatus of claim 3, wherein the circuitry is further configured to cause the display device to provide a user selectable indication associated with reset of a displayed trajectory of the object.

7. The apparatus of claim 1, wherein the first visual information includes at least one of an image, a figure, a video, or a picture.

8. The apparatus of claim 1, wherein the first visual information and the second visual information are displayed in a synchronous relationship so as to show a time-based relationship between the first visual information and the second visual information.

9. The apparatus of claim 8, wherein the second visual information is associated with an object trajectory, and the first visual information is associated with a change of a state of at least one of a user hand or a user wrist.

10. The apparatus of claim 9 wherein the object trajectory is a trajectory of a tennis racket.

11. A method, comprising:
acquiring first data from a first sensor attached to a first body part of a user, and second data from a second sensor attached to a second body part of the user;
sending, by a communications interface, the first data and the second data to analysis circuitry,
wherein the analysis circuitry adjusts a delay of at least one of the first data or the second data for analysis of a body movement of the user, wherein the adjustment is based on a time stamp issued to each of the first data and the second data, and wherein the analysis circuitry determines a time-series change of angles of the first body part to represent the body movement, based on the first data, the second data, and the adjusted delay;
receiving a display signal from the analysis circuitry; and
displaying first visual information regarding the time-series change of the angles, and second visual information regarding the body movement so as to visualize the body movement, wherein the first visual information and the second visual information are displayed based on the display signal, and wherein the first visual information is different from the second visual information.

12. The method of claim 11, wherein the first visual information is based on analysis of the body movement of the user.

13. The method of claim 11, wherein the first visual information includes a trajectory, of an object based on a user swing, as part of the body movement of the user.

14. The method of claim 11, wherein the first visual information includes a change in a state of at least one of the first body part or the second body part.

15. The method of claim 14 further comprising:
displaying a user selectable indication that identifies a selected body part that is associated with the change in the state; and
displaying the first visual information, based on a selection of the user selectable indication, regarding the change in the state of the selected body part.

16. The method of claim 13, further comprising displaying a user selectable indication associated with reset of a displayed trajectory of the object.

17. The method of claim 11, wherein the first visual information includes at least one of an image, a figure, a video, or a picture.

18. The method of claim 11, further comprising displaying the first visual information and the second visual information in a synchronous relationship so as to show a time-based relationship between the first visual information and the second visual information.

19. An apparatus, comprising:
a display device;
a communications interface configured to receive first data from a first sensor attached to a first body part of a user, and a second data from a second sensor attached to a second body part of the user; and
circuitry configured to:
adjust a delay of at least one of the first data or the second data for analysis of a body movement of the user, wherein the adjustment is based on a time stamp issued to each of the first data and the second data;
determine a time-series change of angles of the first body part to represent the body movement, based on the first data, the second data, and the adjusted delay; and
generate a display signal that causes the display device to generate first visual information regarding the time-series change of the angles, and second visual information regarding the body movement,
wherein the generation of the display signal is based on at least one of the first data or the second data,
wherein the first visual information is different from the second visual information, and
wherein the display device is configured to display the first visual information and the second visual information.

20. The apparatus of claim 19, wherein the first visual information is based on analysis of the body movement of the user.

* * * * *